United States Patent
Habus et al.

(10) Patent No.: US 9,926,269 B2
(45) Date of Patent: Mar. 27, 2018

(54) BETA-LACTAM CHOLESTEROL ABSORPTION INHIBITORS

(71) Applicant: Rudjer Boskovic Institute, Zagreb (HR)

(72) Inventors: Ivan Habus, Zagreb (HR); Tonko Drazic, Zagreb (HR)

(73) Assignee: RUDJER BOSKOVIC INSTITUTE, Zagreb (HR)

( * ) Notice: Subject to any disclaimer, the term of this patent is extended or adjusted under 35 U.S.C. 154(b) by 0 days.

(21) Appl. No.: 15/105,282

(22) PCT Filed: Dec. 16, 2014

(86) PCT No.: PCT/HR2014/000043
§ 371 (c)(1),
(2) Date: Jun. 16, 2016

(87) PCT Pub. No.: WO2015/092448
PCT Pub. Date: Jun. 25, 2015

(65) Prior Publication Data
US 2016/0355473 A1    Dec. 8, 2016

Related U.S. Application Data

(60) Provisional application No. 61/917,371, filed on Dec. 18, 2013.

(51) Int. Cl.
| | | |
|---|---|---|
| *C07D 205/085* | (2006.01) | |
| *A61K 9/20* | (2006.01) | |
| *A61K 9/48* | (2006.01) | |
| *A61K 31/397* | (2006.01) | |

(52) U.S. Cl.
CPC ........ *C07D 205/085* (2013.01); *A61K 9/2072* (2013.01); *A61K 9/4808* (2013.01); *A61K 31/397* (2013.01)

(58) Field of Classification Search
None
See application file for complete search history.

(56) References Cited

FOREIGN PATENT DOCUMENTS

WO   PCT/US1995/007117 A1   12/1995
WO   WO1995035277 A1 *   12/1995   ........... C07D 208/08

OTHER PUBLICATIONS

The American Heart Association. Prevention and Treatment of High Cholesterol. (2014) Web < http://www.heart.org/HEARTORG/Conditions/Cholesterol/PreventionTreatmentofHighCholesterol/Prevention-and-Treatment-of-High-Cholesterol_UCM_001215_Article.jsp#>.*
Hoffman, Matthew. WebMD. Atherosclerosis: Prevention Through the Ages. (2016) Web < http://www.webmd.com/heart/features/atherosclerosis-prevention-through-ages#1>.*
Poljak, Tanja. Croatica Chemica Acta 81 (4) 539-558 (2008).*
Jarrahpour, Aliasghar. Bull Chem. Soc. Jpn. 84 (3) 320-327 (2011).*
Drugs.com. Enteric Coated Tablet. (2009) Web >https://web.archive.org/web/20090602162551/http://www.drugs.com/dict/enteric-coated-tablet.html>.*
Ojima, I and Habus, I., Asymmetric Synthesis of Beta-Lactams by Chiral Ester Enolate-Imine Condensation, Tetrahedron Letters, vol. 31, No. 30, pp. 4289-4292 (1990). Perganon Press, plc (Great Britain).
International Search Report in PCT/HR2014/000043 (dated 2015).
Written Opinion in PCT/HR2014/000043 dated Jun. 21, 2016.
International Preliminary Report on Patentability in PCT/HR2014/000043 dated Jun. 21, 2016.

* cited by examiner

*Primary Examiner* — Deepak R Rao
*Assistant Examiner* — Laura M Daniel
(74) *Attorney, Agent, or Firm* — Ted Whitlock (57) ABSTRACT

The present invention relates to the novel compounds represented by Formula (Ia) or (Ib) and to their pharmaceutical preparations for the treatment of atherosclerosis and cholesterol level reduction.

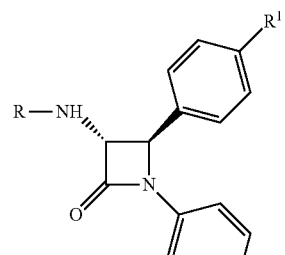

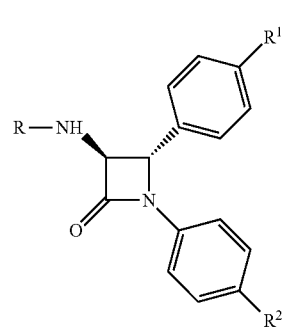

21 Claims, 2 Drawing Sheets

BETA-LACTAM CHOLESTEROL ABSORPTION INHIBITORS

FIELD OF THE INVENTION

The invention is directed to a certain amino-β-lactam derivatives and their use in the reduction of cholesterol level.

BACKGROUND OF THE INVENTION

Cardiovascular disease (like atherosclerosis) represents the primary cause of mortality in developed countries. It has been shown that a lipid disorder, such as high blood cholesterol and triglycerides, increases the risk for atherosclerosis, and thus for heart disease, stroke, high blood pressure and other pathological conditions. One key strategy for reducing the risk of atherosclerosis has been to lower the blood cholesterol levels.

The most of the cholesterol found in humans is produced by the body. Cholesterol is unable to dissolve in the blood and must therefore be transported to and from cells by lipoprotein carriers. Low-density lipoprotein (LDL) is known as "bad" cholesterol. High-density lipoprotein (HDL) is known as "good" cholesterol. These two types of lipids, along with triglycerides and Lp(a) cholesterol, make up the total blood cholesterol count. An elevated LDL blood cholesterol level (hypercholesterolemia) may lead to slow build up cholesterol deposits in the walls of the arteries feeding the heart and brain, forming a plaque which can clog these arteries, a condition known as atherosclerosis. A clot (thrombus) that forms near this plaque can block the blood flow to a part of the heart muscle and cause a heart attack. As well as if such a clot blocks the blood flow to a part of the brain, a stroke results.

Cholesterol levels in many people can be controlled by diet, but for many patients diet changes alone are insufficient to reduce high cholesterol. Treatment options may include lipid-regulating medications, such as statins (simvastatin, atorvastatin), that act to lower LDL cholesterol. These drugs, however, are associated with significant adverse side effects. Additional therapies may include the use of lipid-lowering compounds such as ezetimibe that selectively inhibit the intestinal cholesterol absorption (WO9508532; Rosenblum et. al. *J. Med. Chem.* 1998, 41, 973).

Ezetimibe analogues have also been reported to inhibit the cholesterol absorption (Xu et. al. *Bioorg. Med. Chem. Lett.* 2007, 17, 101).

Several other 2-azetidinone derivatives have been reported as being useful in lowering cholesterol.

EP1522541A1 discloses heterocyclic compounds including 2-azetidinones useful in the treatment and prevention of atherosclerosis and for the reduction of cholesterol levels. U.S. Pat. No. 7,470,678B2 discloses diphenylazetidinone derivatives for treating disorders of the lipid metabolism. U.S. Pat. No. 5,767,115A relates to hydroxy-substituted azetidinone compounds useful as hypocholesterolemic agents.

Although it has been proved that ezetimibe decreases cholesterol levels, its efficacy on decreasing atherosclerotic or vascular events remains questionable. (Mitka M (May 2008). "Cholesterol drug controversy continues". JAMA 299 (19): 2266).

Therefore, there remains a need for additional safer and more effective therapeutics to lower cholesterol as a way to prevent and/or treat cardiovascular diseases and conditions.

SUMMARY OF THE INVENTION

The present invention relates to trans-(3R,4R)- or trans-(3S,4S)-2-azetidinone represented by Formula (Ia) or (Ib):

wherein R represents
a) hydrogen;
b) —C(=O)—$C_{1-6}$alkyl-$C_6H_4R^3$, —C(=O)—$C_{1-6}$alkenyl-$C_6H_4R^3$ or —C(=O)—$C_6H_4R^3$;
c) —$C_{1-6}$alkyl-$C_6H_4R^3$ or —$C_{1-6}$alkenyl-$C_6H_4R^3$, wherein said —$C_{1-6}$alkyl or —$C_{1-6}$alkenyl is substituted by OH;
$R^1$ represents OH or —OMe;
$R^2$ represents a halogen or —OMe;
$R^3$ represents hydrogen, a halogen, —OMe, —$NO_2$ or —OH;
or a salt thereof.

The present invention also relates to pharmaceutical composition comprising the compounds of Formula (Ia) or (Ib) or the pharmaceutically acceptable salts thereof.

The present invention further relates to pharmaceutical composition comprising an enteric coating that prevents release and absorption of active ingredients until they reach the intestine.

Furthermore the present invention relates to the compounds of Formula (Ia) or (Ib) or the pharmaceutically acceptable salts thereof for use in medical therapy.

According to another aspect, the invention relates to the compounds of Formula (Ia) or (Ib) or the pharmaceutically acceptable salts thereof for use in the reduction of cholesterol levels.

DESCRIPTION OF THE EMBODIMENTS

It will be understood that the present invention covers all combinations of aspects, suitable, convenient and preferred groups described herein.

The present invention includes both the individual enantiomers or diastereoisomers and the corresponding racemates or diastereoisomeric mixtures of the compounds according to the invention and their respective salts.

In the context of the present invention, the substituents, if not stated otherwise, in general have the following meaning:

The term "alkyl" as used herein, refers to a saturated, straight or branched-chain hydrocarbon radical containing the stated number of carbon atoms. For example, —$C_{1-6}$ alkyl refers to an alky group having from 1 to 0.6 carbon atoms. Examples of "—$C_{1-6}$alkyl" radicals include: methyl, ethyl, propyl (n-propyl and isopropyl), butyl (n-butyl, isobutyl and t-butyl), pentyl (n-pentyl, isopentyl, and neopentyl), hexyl and the like.

The term "alkenyl" as used herein refers to an unsaturated linear or branched hydrocarbon group containing one or more carbon-carbon double bonds and having the stated number of carbon atoms. Examples of "—$C_{2-4}$alkenyl" include ethenyl, propenyl, butenyl and the like. The term "halogen" or "halo" refers to fluorine, chlorine, bromine or iodine atom.

The term "substituted —$C_{1-6}$alkyl" or "—$C_{1-6}$alkyl substituted by" as used herein refers to —$C_{1-6}$alkyl wherein a hydrogen on one of the —$CH_2$— units of the —$C_{1-6}$alkyl is substituted by stated group.

In one aspect, compounds of the present invention may be in the form of pharmaceutically acceptable salts, solvates or solvates of salts. In a further aspect, a compound of Formula (I) of the present invention may be in the form of a pharmaceutically acceptable salt.

In one aspect, the present invention relates to trans-(3R, 4R)-2-azetidinone represented by Formula (Ia):

wherein R represents
a) hydrogen;
b) —C(=O)—$C_{1-6}$alkenyl-$C_6H_4R^3$ or —C(=O)—$C_{1-6}$alkenyl-$C_6H_4R^3$ or —C(=O)—$C_6H_4R^3$;
c) —$C_{1-6}$alkyl-$C_6H_4R^3$ or —$C_{1-6}$alkenyl-$C_6H_4R^3$, wherein said —$C_{1-6}$alkyl or —$C_{1-6}$alkenyl is substituted by OH;
$R^1$ represents OH or —OMe;
$R^2$ represents a halogen or —OMe;
$R^3$ represents hydrogen, a halogen, —OMe, —$NO_2$ or —OH;
or a salt thereof.

In another aspect, the present invention relates to trans-(3S,4S)-2-azetidinone represented by Formula (Ib):

wherein R represents
a) hydrogen;
b) —C(=O)—$C_{1-6}$alkyl-$C_6H_4R^3$, —C(=O)—$C_{1-6}$alkenyl-$C_6H_4R^3$ or —C(=O)—$C_6H_4R^3$;
c) —$C_{1-6}$alkyl-$C_6H_4R^3$ or —$C_{1-6}$alkenyl-$C_6H_4R^3$, wherein said —$C_{1-6}$alkyl or —$C_{1-6}$alkenyl is substituted by OH;
$R^1$ represents —OH or —OMe;
$R^2$ represents a halogen or —OMe;
$R^3$ represents hydrogen, a halogen, —OMe, —$NO_2$ or —OH;
or a salt thereof.

In one aspect, the present invention is directed to a compound of Formula (Ia) wherein $R^1$ represents OH.

In one aspect, the present invention is directed to a compound of Formula (Ib) wherein $R^1$ represents OH.

In one aspect, the present invention is directed to a compound of Formula (Ia) wherein $R^2$ represents a halogen. In further aspect $R^2$ represents fluorine.

In one aspect, the present invention is directed to a compound of Formula (Ib) wherein $R^2$ represents a halogen. In further aspect $R^2$ represents fluorine.

In one aspect, the present invention is directed to a compound of Formula (Ia) wherein R represents hydrogen.

In one aspect, the present invention is directed to a compound of Formula (Ib) wherein R represents hydrogen.

In one aspect, the present invention is directed to a compound of Formula (Ia) wherein R represents —C(=O)—$C_{1-6}$alkyl-$C_6H_4R^3$. In further aspect R represents —C(=O)—$CH_2$—$C_6H_4R^3$ wherein $R^3$ is hydrogen or a halogen. In yet further aspect R represents —C(=O)—$CH_2$—$C_6H_4F$.

In one aspect, the present invention is directed to a compound of Formula (Ib) wherein R represents —C(=O)—$C_{1-6}$alkyl-$C_6H_4R^3$. In further aspect R represents —C(=O)—$CH_2$—$C_6H_4R^3$ wherein $R^3$ is hydrogen or a halogen. In yet further aspect R represents —C(=O)—$CH_2$—$C_6H_4F$.

In one aspect, the present invention is directed to a compound of Formula (Ia) wherein R represents —C(=O)—$C_{1-6}$alkenyl-$C_6H_4R^3$. In further aspect R represents —C(=O)—CH=CH—$C_6H_4R^3$ wherein $R^3$ is hydrogen or a halogen. In yet further aspect R represents —C(=O)—CH=CH—$C_6H_4F$.

In one aspect, the present invention is directed to a compound of Formula (Ib) wherein R represents —C(=O)—C$_{1-6}$alkenyl-C$_6$H$_4$R$^3$. In further aspect R represents —C(=O)—CH=CH—C$_6$H$_4$R$^3$ wherein R$^3$ is hydrogen or a halogen. In yet further aspect R represents —C(=O)—CH=CH—C$_6$H$_4$F.

In one aspect, the present invention is directed to a compound of Formula (Ia) wherein R represents —C(=O)—C$_6$H$_4$R$^3$. In further aspect R represents —C(=O)—C$_6$H$_4$R$^3$ wherein R$^3$ is hydrogen or a halogen. In yet further aspect R represents —C(=O)—C$_6$H$_4$F.

In one aspect, the present invention is directed to a compound of Formula (Ib) wherein R represents —C(=O)—C$_6$H$_4$R$^3$. In further aspect R represents —C(=O)—C$_6$H$_4$R$^3$ wherein R$^3$ is hydrogen or a halogen. In yet further aspect R represents —C(=O)—C$_6$H$_4$F.

In one aspect, the present invention is directed to a compound of Formula (Ia) wherein R represents —C$_{1-6}$alkyl-C$_6$H$_4$R$^3$ and C$_{1-6}$alkyl is substituted by OH. In further aspect R represents —CH$_2$—CH(OH)—C$_6$H$_4$R$^3$ wherein R$^3$ is hydrogen or a halogen. In yet further aspect R represents —CH$_2$—CH(OH)—C$_6$H$_4$F.

In one aspect, the present invention is directed to a compound of Formula (Ib) wherein R represents —C$_{1-6}$alkyl-C$_6$H$_4$R$^3$ and —C$_{1-6}$alkyl is substituted by OH. In further aspect R represents —CH$_2$—CH(OH)—C$_6$H$_4$R$^3$ wherein R$^3$ is hydrogen or a halogen. In yet further aspect R represents —CH$_2$—CH(OH)—C$_6$H$_4$F.

In one aspect, the present invention comprises a compound of Formula (Ia) selected from:
(3R,4R)-3-amino-1-(4-fluorophenyl)-4-(4-hydroxyphenyl) azetidin-2-one (1);
(E)-1-[(3R,4R)-1-(4-fluorophenyl)-4-(4-hydroxyphenyl)-2-oxo-3-azetidinylamino]-3-phenyl-2-propen-1-one (2);
(E)-1-[(3R,4R)-1-(4-fluorophenyl)-4-(4-hydroxyphenyl)-2-oxo-3-azetidinylamino]-3-(4-fluorophenyl)-2-propen-1-one (3);
1-[(3R,4R)-1-(4-fluorophenyl)-4-(4-hydroxyphenyl)-2-oxo-3-azetidinylamino]-2-phenyl-ethan-1-one (4);
1-[(3R,4R)-1-(4-fluorophenyl)-4-(4-hydroxyphenyl)-2-oxo-3-azetidinylamino]-2-(4-fluorophenyl)-ethan-1-one (5);
[(3R,4R)-1-(4-fluorophenyl)-4-(4-hydroxyphenyl)-2-oxo-3-azetidinylamino]phenylformaldehyde (6);
[(3R,4R)-1-(4-fluorophenyl)-4-(4-hydroxyphenyl)-2-oxo-3-azetidinylamino](4-fluorophenyl)formaldehyde (7);
(3R,4R)-3-[(2R)-2-(4-fluorophenyl)-2-hydroxyethylamino]-1-(4-fluorophenyl)-4-(4-hydroxyphenyl)azetidin-2-one (8);
(3R,4R)-3-[(2S)-2-(4-fluorophenyl)-2-hydroxyethylamino]-1-(4-fluorophenyl)-4-(4-hydroxyphenyl)azetidin-2-one (9);
(3R,4R)-3-[(2R/S)-2-(4-fluorophenyl)-2-hydroxyethylamino]-1-(4-fluorophenyl)-4-(4-hydroxyphenyl)azetidin-2-one, (8/9-70/30);
(3R,4R)-3-[(2S/R)-2-(4-fluorophenyl)-2-hydroxyethylamino]-1-(4-fluorophenyl)-4-(4-hydroxyphenyl)azetidin-2-one, (9/8-85/15);
or a salt thereof.

In one aspect, the present invention comprises a compound of Formula (Ia) selected from:
N-[(3R,4R)-1-(4-fluorophenyl)-4-(4-hydroxyphenyl)-2-oxo-3-azetidinyl]-(2R)-2-hydroxy-2-(4-fluorophenyl)ethylammonium chloride (10);
N-[(3R,4R)-1-(4-fluorophenyl)-4-(4-hydroxyphenyl)-2-oxo-3-azetidinyl]-(2S)-2-hydroxy-2-(4-fluorophenyl)ethylammonium chloride (11);
N-[(3R,4R)-1-(4-fluorophenyl)-4-(4-hydroxyphenyl)-2-oxo-3-azetidinyl]-(2R/S)-2-hydroxy-2-(4-fluorophenyl) ethylammonium chloride, (10/11-70/30);
N-[(3R,4R)-1-(4-fluorophenyl)-4-(4-hydroxyphenyl)-2-oxo-3-azetidinyl]-(2S/R)-2-hydroxy-2-(4-fluorophenyl) ethylammonium chloride, (11/10-85/15).

The present invention also encompasses solvates (preferably hydrates) of the compounds of Formula (Ia) or (Ib) or their salts.

The pharmaceutically suitable salts of the compounds representing a subject of the present invention include the ammonium, calcium, magnesium, potassium, and sodium salts, and those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

Compounds of the present invention inhibit the cholesterol uptake.

Therefore these compounds have potential utility in the treatment and/or prevention of atherosclerosis and of cholesterol level reduction.

In one aspect, the present invention provides a method of cholesterol level reduction.

In another aspect, the present invention provides a method of atherosclerosis treatment.

In yet another aspect, the present invention provides a method of atherosclerosis prevention.

In one aspect, the present invention provides a method for treatment and/or prevention of atherosclerosis, comprising administration to a mammal in need of such treatment an effective amount of a compound of Formula (Ia) or (Ib) or a pharmaceutically acceptable salt thereof.

In one aspect, the present invention provides a method for cholesterol level reduction comprising administration to a mammal in need of such treatment an effective amount of a compound of Formula (Ia) or (Ib) or a pharmaceutically acceptable salt thereof.

In one aspect, the present invention provides a compound of Formula (Ia) or (Ib) or a pharmaceutically acceptable salt thereof for use in medical therapy.

In one aspect, the present invention provides a compound of Formula (Ia) or (Ib) or a pharmaceutically acceptable salt thereof, for use in the treatment and/or atherosclerosis prevention.

In one aspect, the present invention provides a compound of Formula (Ia) or (Ib) or a pharmaceutically acceptable salt thereof, for use in the cholesterol level reduction.

In further aspect of the invention, the present invention provides the use of a compound of Formula (Ia) or (Ib) or a pharmaceutically acceptable salt thereof in the manufacture of a medicament for the treatment of and/or prevention of atherosclerosis and cholesterol level reduction.

The present invention is also directed to the pharmaceutical compositions comprising a compound of Formula (Ia) or (Ib) or a pharmaceutically acceptable salt thereof in an amount effective for therapeutic treatment of atherosclerosis and the cholesterol level reduction.

The present invention is further related to a pharmaceutical composition for the atherosclerosis treatment and the cholesterol level reduction comprising a compound of Formula (Ia) or (Ib) or a pharmaceutically acceptable salt thereof.

The present invention further relates to a pharmaceutical composition comprising an enteric coating that prevents release and absorption of active ingredients until they reach the intestine.

In one aspect, the present invention relates to a pharmaceutical composition comprising a compound of Formula (Ia) or (Ib) or a pharmaceutically acceptable salt thereof.

In another aspect, the present invention relates to a combination of a compound of Formula (Ia) or (Ib) or a pharmaceutically acceptable salt thereof with one or more lipid-regulating medications such as statins (e.g. simvastatin, atorvastatin). The combinations referred to the above may conveniently be presented for use in the form of a pharmaceutical composition and thus pharmaceutical compositions comprising a combination as defined above together with one or more pharmaceutically acceptable carriers thereof represent a further aspect of the invention.

The individual components of such combinations may be administered either sequentially or simultaneously in separate or combined pharmaceutical formulations. The appropriate doses of known therapeutic agents will be readily appreciated by those skilled in the art.

Pharmaceutical Compositions

It will be appreciated that pharmaceutical compositions for use in accordance with the present invention may be in the form of oral, parenteral, sublingual or enterally administered suspensions, solutions, capsules or tablets which may be formulated in conventional manner using one or more pharmaceutically acceptable carriers or excipients. Pharmaceutical compositions containing the compounds of the present invention may be in any form suitable for the intended method of administration.

Accordingly, the present invention provides a pharmaceutical composition comprising of a) a compound of Formula (Ia) or (Ib) or a pharmaceutically acceptable salt thereof and b) one or more pharmaceutically acceptable carriers.

Pharmaceutical compositions can be prepared by mixing a therapeutically effective amount of the active substance with a pharmaceutically acceptable carrier that can have different forms, depending on the way of administration. The preparation of the pharmaceutical composition can include mixing, granulating, tableting and dissolving the ingredients.

The term "carrier" refers to a diluent, excipient, and/or vehicle with which an active compound is administered. The pharmaceutical compositions of the invention may contain combinations of more than one carrier. Carriers can be in solid or liquid form. Solid carriers can be lactose, sucrose, talc, gelatin, agar, pectin, magnesium stearate, fatty acids etc. Liquid carriers can be sterile liquids, such as water, saline solutions, aqueous dextrose solutions, aqueous glycerol solutions, and oils including those of petroleum, animal, vegetable or synthetic origin, such as peanut oil, soybean oil, mineral oil, sesame oil, olive oil, soybean oils and the like. Carriers may also contain a component for a sustained release of the active component such as glyceryl monostearate or glyceryl distearate. The choice of pharmaceutical carrier can be selected with regard to the intended route of administration and standard pharmaceutical practice. The pharmaceutical compositions may comprise, in addition to the carrier, any suitable binder(s), lubricant(s), suspending agent(s), coating agent(s), and/or solubilizing agent(s).

The term "pharmaceutically acceptable", as used herein, refers to salts, molecular entities and other ingredients of compositions that are generally physiologically tolerable and do not typically produce untoward reactions when administered to a mammal (e.g., human). Suitably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

In one aspect, the pharmaceutical composition is formulated for oral administration. The compounds of the invention can be administered for immediate-, delayed-, modified-, sustained-, pulsed- or controlled-release applications. Pharmaceutical compositions can be prepared by using conventional pharmaceutical excipients and methods of preparation. All excipients may be mixed with disintegrating agents, solvents, granulating agents, moisturizers and binders. The forms for oral administration can be capsules, granules, powders or tablets. Tablets and capsules are the preferred oral composition forms.

In one preferred aspect, the pharmaceutical composition is formulated for oral sustained-release applications. Such formulation includes an enteric coating that prevents release and absorption of active ingredients until they reach the intestine.

In one aspect, the pharmaceutical composition includes an enteric coating known in the art, for example as described in Hong Wen and Kinam Park. *Oral Controlled Release Formulation Design and Drug Delivery: Theory to practice* (pages 206-208). New Jersey: John Wiley & Sons, 2010 and Raymond C. Rowe, Paul J. Sheskey, Paul J. Weller. *Handbook of Pharmaceutical Excipients*. Sixth ed., London: Pharmaceutical Press, 2009.

Useful oral application forms include application forms which release the active component in modified form, such as for example enteric coating tablets or capsules containing coated granules.

"Enteric coating tablet" means a tablet which is coated with a material to prevent or minimize dissolution in the stomach but allow dissolution in the small intestine.

Enteric coating which will not dissolve in the stomach acidic juices (pH~3), but will rather dissolve in the intestine alkaline environment may include fatty acids, waxes, shellac, plastics, and plant fibers cellulose acetate phthalate, hypromellose phthalate, hypromellose acetate succinate, polymethacrylates, polyvinyl acetate phthalate.

Parenteral application can be carried out with avoidance of an absorption step (e.g. intravenously) or with inclusion of an absorption (e.g. intramuscularly, subcutaneously, intraperitoneally). Useful parenteral application forms include injection and infusion preparations in the form of solutions, suspensions, emulsions, lyophilisates and sterile powders.

The therapeutic doses will generally be between about 0.01 and 2000 mg/day, and suitably between about 0.1 and 500 mg/day. Other doses may be used, and they may be administered in one to four daily doses, for example, depending on the route of administration, clinical phase of the disease or disorder, and the condition of the subject.

Biological Assays

The potential of the compounds in the present invention is to provide therapeutic benefits in the cholesterol level reduction and to exhibit low cytotoxicity that may be demonstrated, for example, using the following in vitro assays.

Ezetimibe, used in biological testing as the standard compound, is obtained commercially or is synthesized according to Wu et al. *J. Org. Chem.* 1999, 64, 3714.

Cell Culture and Establishment of Cell Line Stably Line Expressing hNPC1L1 Protein.

Madin-Darby Canine Kidney H (MDCKII), MDCKII cells stably expressing human NPC1L1 (hNPC1L1/MDCKII) and HepG2 cells were maintained in DMEM (Dulbecco's Modified Eagle Medium) containing 100 units/mL penicillin and 100 μg/mL streptomycin supplemented with 10% FCS. The cells were grown at 37° C. in a humidified 5% CO$_2$ incubator. Stable transfection of MDCKII cells with human NPC1L1 protein was performed using the Lipofectamine LTX (Invitrogen, USA) according to the manufecturer's protocol. Selection with 1000 µg/mL G418 (Sigma-Aldrich, Germany) was started 2 days after transfection. The concentration of G418 was decreased to 500 µg/mL after 14 days. Transfected cells were maintained in DMEM (Dulbecco's Modified Eagle Medium) containing 100 units/mL penicillin and 100 µg/mL streptomycin supplemented with 10% FCS and 500 µg/mL G418.

Medium Preparation.

Cholesterol Depleting Medium (Medium A) was DMEM (Dulbecco's Modified Eagle Medium) containing 100 units/mL penicillin and 100 µg/mL streptomycin supplemented with 5% LPDS. Cholesterol Replenishing Medium (Medium B) was prepared according to the modified method reported by Field et. al. *J. Lipid Res.* 1991, 32, 1811. In brief, 0.25 mM oleic acid, 50 µM free cholesterol, 10 µM compactin, 50 µM mevalonate, 5 mM Na-taurocholate and [$^3$H] cholesterol (0.18 µCi/mL medium) in Medium A were mixed and sonicated. Following the micellar formation, compounds (73 mM Stock in DMSO) were added to Medium B in order to obtain the final concentrations (10, 30, 60, 90, 120, 150, 200 µM) and the medium was vortexed.

Cholesterol Uptake Assay.

Figure 1:
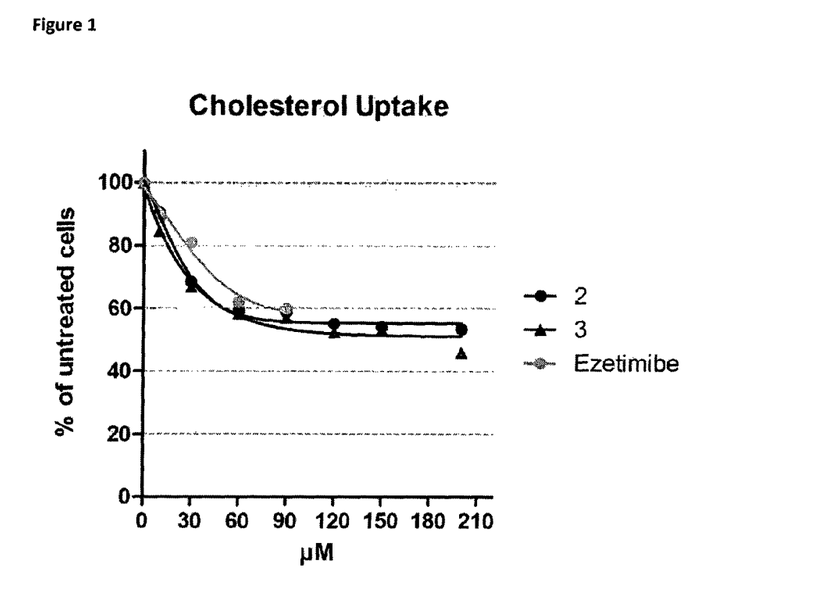
FIG. 1 shows the cholesterol uptake in the cells treated with compounds 2 and 3 compared to cholesterol uptake in the cells treated with ezetimibe.
Figure 2:
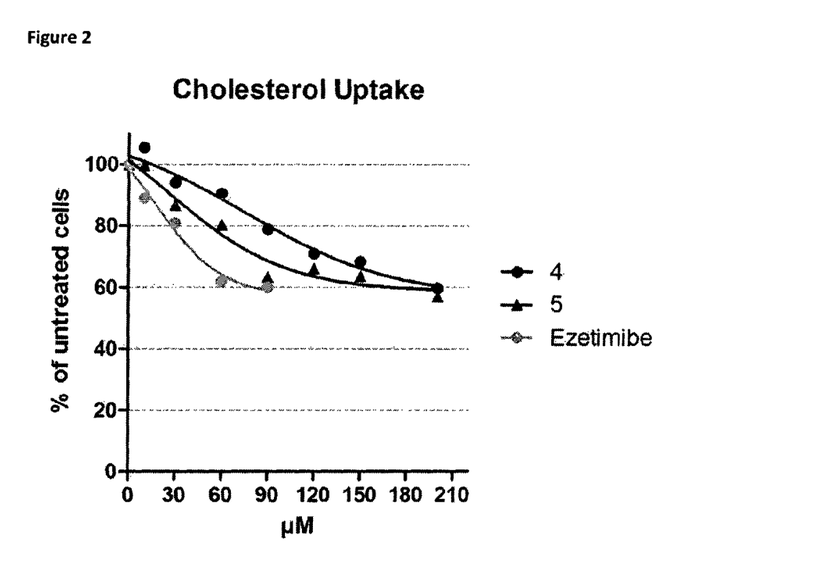
FIG. 2 shows the cholesterol uptake in the cells treated with compounds 4 and 5 compared to cholesterol uptake in the cells treated with ezetimibe.
Figure 3:
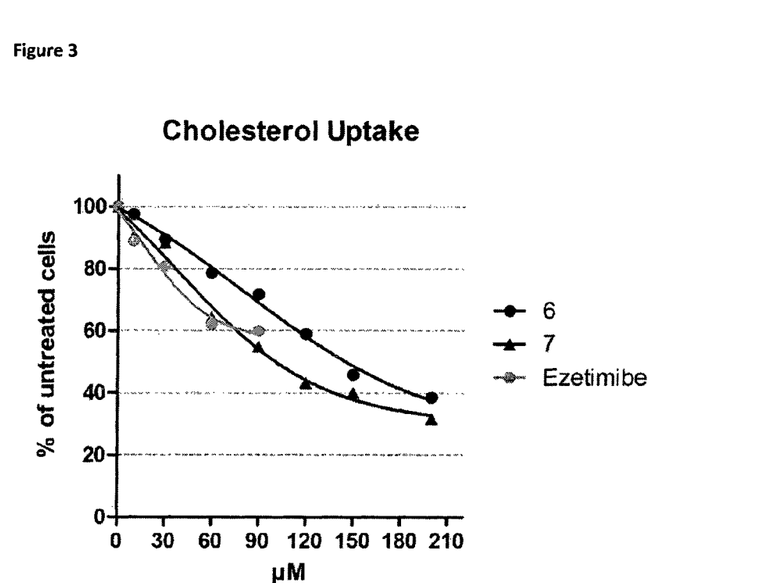
FIG. 3 shows the cholesterol uptake in the cells treated with compounds 6 and 7 compared to cholesterol uptake in the cells treated with ezetimibe.
Figure 4:
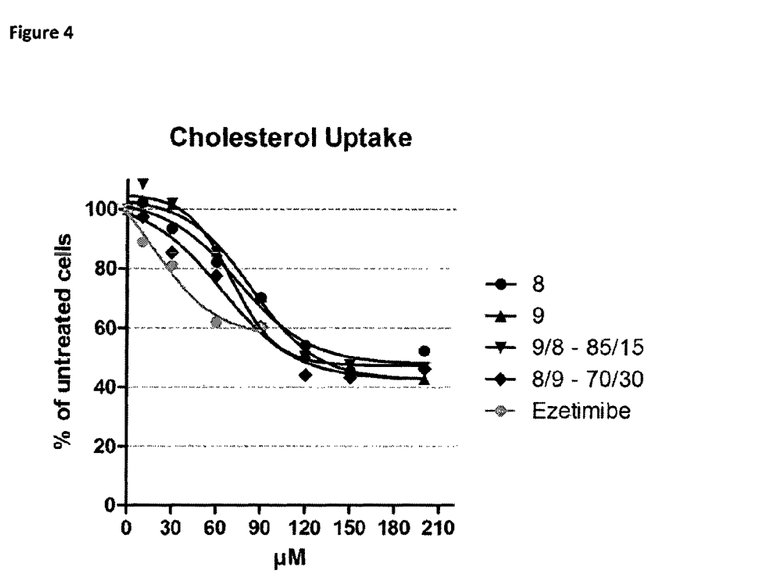
FIG. 4 shows the cholesterol uptake in the cells treated with compounds 8, 9, diastereoisomeric mixtures 8/9 in ratio 70:30 and 9/8 in ratio 85:15 compared to cholesterol uptake in the cells treated with ezetimibe.

MDCKII wild type or hNPC1L1/MDCKII cells were seeded in 24-well plates at a density of 5×10$^5$ cells/mL medium (500 µL medium/well) in Medium A 24 h before the treatment. Cells were washed once with PBS and incubated in Medium B (500 µL medium/well) containing micelles and tested compound in indicated concentrations for 1 h. Following the incubation, medium was removed and cells were washed three times with ice cold 0.2% BSA fatty acid free. Cells were then lysed and 100 µL of the lysate was taken for liquid scintillation counting. Protein concentrations of the lysates were determined with Protein Assay kit (Bio-Rad). The results were expressed as percent uptake of untreated cells. Each concentration was tested in duplicate in three independent experiments (FIGS. 1-4).

In Vivo Acute Inhibition of Cholesterol Absorption.

Male C57BL/6 mice 25-28 weeks of age were maintained in a temperature controlled environment under a 12 h light/12 h dark cycle with free access to chow diet and water. Mice were treated for 2 days with either vehicle or indicated concentration of compounds dissolved in corn oil (100 µL). The compounds were administered to mice by oral gavaging after 4 h fasting. On day 2, 90 minutes post compound treatment, mice were gavaged with corn oil (200 µL) containing [$^3$H]cholesterol (2 µCi). After 4 h mice were sacrificed and plasma, liver and small intestine divided in three equal parts (duodenum, jejunum and ileum) were collected. Tissues were lyophilized and digested in 1 M NaOH (1 mL) overnight at 65° C. and radioactivity was measured by liquid scintillation counting.

Cytotoxicity Assay.

For the cytotoxicity determination, MDCKII, hNPC1L1/MDCKII and HepG2 cells were seeded in 96-well microtiter plates on day 0 at the density of 3000 cells/well. On day 1, tested compounds (73 mM Stock in DMSO) were added in five consecutive 10-fold dilutions (10$^{-8}$ to 10$^{-4}$ mol/L) and incubated for 72 h. The compound cytotoxicity was assessed on day 4 performing the MTT cell proliferation assay (Sigma-Aldrich, Germany) which detects mitochondrial dehydrogenase activity in viable cells. (Mosmann, T. *J. Immunol. Methods* 1983, 65, 55.) The results are expressed as LC$_{50}$ and the values for each compound were calculated from dose-response curves using linear regression analysis. Each concentration was tested in quadruplicate in three independent experiments (Table 1).

TABLE 1

Compound cytotoxicity results obtained in in vitro testing.

| Compound | MDCKII LC$_{50}$ µM | hNPC1L1MDCKII LC$_{50}$ µM | HepG2 LC$_{50}$ µM |
|---|---|---|---|
| Ezetimibe | >100 | 62.29 | 69.74 |
| 2 | 66.55 | 65.06 | 63.27 |
| 3 | 63.95 | 63.27 | 57.47 |
| 4 | >100 | >100 | >100 |
| 5 | >100 | >100 | >100 |
| 6 | 91.23 | 68.34 | 67.58 |
| 7 | 78.64 | 64.69 | 71.93 |
| 8 | >100 | >100 | >100 |
| 9 | >100 | >100 | >100 |
| 8/9-70/30 | >100 | >100 | >100 |

Methods of Preparation.

The compounds of Formula (Ia) or (Ib) and salts thereof may be prepared by general methods outlined hereinafter, said method constituting a further aspect of the present invention. In the following description, the groups R, R$^1$, R$^2$ and R$^3$ have the meaning defined for the compounds of Formula (Ia) or (Ib) unless otherwise stated.

It will be appreciated by those skilled in the art that it may be desirable to use protected derivatives of intermediates used in the preparation of the compounds of Formula (Ia) or (Ib). Protection and deprotection of functional groups may be performed by methods known in the art.

For example, —OH group may be protected by t-butyldimethylsilyl by reaction with TBDMSCl which may be removed under acid condition or by treatment with (n-butyl)$_4$ N$^+$F$^-$.

The each final product is purified, as necessary, using standard techniques such as silica gel column chromatography and the like (e.g. preparative thin-layer chromatography (PTLC), normal and/or reversed phase high performance liquid chromatography (HPLC) applying a variety of chiral or achiral HPLC columns), and/or by recrystallization.

Compounds of Formula (Ia) or (Ib) wherein R is —C(=O)—C$_{1-6}$alkyl-C$_6$H$_4$R$^3$, —C(=O)—C$_{1-6}$alkenyl-C$_6$H$_4$R$^3$ or —C(=O)—C$_6$H$_4$R$^3$ may be prepared from the compound of Formula (Ia) or (Ib) wherein R is hydrogen that is replaced in an acylation reaction with an agent of Formula (II) in an aprotic solvent such as dichlorometane in the presence of Et$_3$N at reflux temperature and dry conditions under argon atmosphere.

R$^3$C$_6$H$_4$-L-C(=O)—Cl    (II)

wherein L is —C$_{1-6}$alkyl-, —C$_{1-6}$alkenyl- or is absent

Compounds of Formula (Ia) or (Ib), wherein R is hydrogen, may be prepared in the reaction of imines of Formula (III) with chiral ester enolate of the compound of Formula (IV) generated in situ in the presence of LDA from N,N-bis-(silyl)glycinates (IVa or IVb) following the procedure as described in Hart et. al. *J. Org. Chem.* 1983, 48, 289; Ha et. al. *J. Am. Chem. Soc.* 1984, 106, 4819; Hart et. al. *Chem. Rev.* 1989, 89, 1447; Ojima et. al. *Tetrahedron Lett.* 1990, 31, 4289. and Poljak et. al. *J. Mol. Struct.* 2005, 751, 60.

Imines III

R¹ = OH, OMe, t-butyldimethylsilyoxy
R² = halogen, OMe

IVa, 1-[(1R,2S,5R)-(-)-(menthyloxycarbonyl)methyl]-
2,2,5,5-tetramethyl-2,5-disilyl-1-azacyclopentane
IVb, 1-[(1S,2R,5S)-(-)-(menthyloxycarbonyl)methyl]-
2,2,5,5-tetramethyl-2,5-disilyl-1-azacyclopentane Compounds of Formula (III) may be obtained starting from the corresponding benzaldehyde of Formula (V) and aromatic amine of Formula (VI), according to a standard procedure for imine synthesis (Layer *Chem. Rev.* 1963, 63, 489; Ojima et. al. *Tetrahedron Lett.* 1990, 31, 4289 and Poljak et. al. *J. Mol. Struct.* 2005, 751, 60.), wherein aldehydes (V) were reacted with amines (VI) in EtOH at room temperature. Free —OH group in imine Formula (III) could be protected with TBDMS in anhydrous dichloromethane and inert atmosphere at 0° C.

V

R¹ = OMe, OH

VI

R² = halogen, OMe

Compounds of Formula (Ia) or (Ib), wherein R is —$C_{1-6}$alkyl-$C_6H_4R^3$ and the —$C_{1-6}$alkyl is substituted with —OH group, may be prepared from the compound of Formula (Ia) or (Ib), wherein R is hydrogen, by an alkylation reaction with an agent of Formula (VII).

$$R^3C_6H_4—C_{1-6}alkyl-Br \quad (VII)$$

wherein one of the —$CH_2$— units in —$C_{1-6}$alkyl is replaced with —C(=O)— group The reaction of N-alkylation proceeded, applying modified literature procedures Hoffman *Philos. Trans.* 1850, CXL, 93 and O'Meara et. al. *J. Org. Chem.* 1998, 63, 3117, in a mixture of anhydrous THF and DMF, in the presence of sodium iodide and $Et_3N$ at room temperature for 3 hours, followed by the subsequent reduction of the carbonyl group in the presence of (R)- or (S)-CBS catalyst and $BH_3.Me_2S$ at −20° C. for 2-20 hours according to the modified Corey's procedure as described in the literature Masui et. al. *Synlett.* 1997, 3, 273, Quallich et. al. *Tetrahedron Lett.* 1993, 34, 785 and Wu et al. *J. Org. Chem.* 1999, 64, 3714. The reaction is allowed to reach room temperature and is quenched with methanol.

Alternatively, compound of Formula (Ia) or (Ib), wherein R is —$C_{1-6}$alkyl-$C_6H_4R^3$ and the —$C_{1-6}$alkyl is substituted with —OH group, may be prepared from the compound of Formula (Ia) or (Ib), wherein R is hydrogen, following our modified N-alkylation procedure described in the literature by Xu et. al. *Bioorg. Med. Chem. Lett.* 2007, 17, 101, with an agent of Formula (VIII). The reaction proceeds in a reaction flask protected from light in a polar aprotic solvent such as acetonitrile at 80° C. for 7 days. t-Butyldimethylsilyl group is subsequently removed under acidic condition or by treatment with (n-butyl)$_4N^+F^-$ to afford free —OH group.

$$R^3C_6H_4—C_{1-6}alkyl-I \quad (VIII)$$

wherein the —$C_{1-6}$alkyl is substituted with t-butyldimethylsilyloxy group

Hydrochloride salts of the compounds of Formula (Ia) or (Ib) may be prepared from their free amines in 1 h treatment at 0° C. with 1M HCl in ethanol followed by evaporation of the solvent to dryness.

Examples

Following abbreviations are used in the text: TBDMSCl for tert-butyldimethylsilyl chloride, DMAP for 4-dimethylaminopyridine, THF for tetrahydrofurane, DMF for dimethylformamide, LDA for lithium diisopropylamide and CBS for Corey-Bakshi-Shibata catalyst, TEAA for tetraethylammonium acetate.

Preparation of
N-(4-hydroxybenzylidene)-4-fluorobenzenamine
(Intermediate 1)

N-(4-hydroxybenzylidene)-4-fluorobenzenamine (Intermediate 1) was synthesized following the procedure described in Layer *Chem. Rev.* 1963, 63, 489; Ojima et. al. *Tetrahedron Lett.* 1990, 31, 4289 and Poljak et. al. *J. Mol. Struct.* 2005, 751, 60. To an ethanol solution of 4-hydroxybenzaldehyde (5 g, 40.94 mmol), 4-fluoroaniline (4.5 g, 40.94 mmol) was added and the mixture was stirred for 3 h. Solvent was evaporated to dryness and the product recrystallized in ethyl acetate. Intermediate 1 was obtained as white crystals (7.6 g, 84%) (Scheme 1).

¹H NMR (600 MHz, DMSO-d₆): 6.88 (d, 2H, J=8.6 Hz), 7.19-7.27 (m, 4H), 7.76 (d, 2H, J=8.6 Hz), 8.46 (s, 1H), 10.12 (bs, 1H).

Scheme 1.

Preparation of N-(4-(t-butyldimethylsilyloxy)benzylidene)-4-fluorobenzenamine (Intermediate 2)

Reaction was carried out in dry conditions under argon atmosphere. To a solution of N-(4-hydroxybenzylidene)-4-fluorobenzenamine (Intermediate 1, 3 g, 14 mmol) in anhydrous $CH_2Cl_2$ (5 mL), a solution of DMAP (85 mg, 0.7 mmol) in anhydrous $CH_2Cl_2$ (1 mL) and $Et_3N$ (2.5 mL, 18.2 mmol) were added. The temperature was decreased to 0° C., reaction mixture stirred for 10 minutes, and a solution of TBDMSCl (2.5 g, 16.8 mmol) in anhydrous $CH_2Cl_2$ (2.5 mL) added dropwise via a syringe. The reaction was maintained at 0° C. for two hours and then warmed to room temperature overnight. Reaction mixture was extracted with 1M NaOH (5×30 mL) in order to remove the remains of unreacted starting material. Collected organic layers were dried over $Na_2SO_4$ and solvent evaporated to dryness. Intermediate 2 was obtained as light brown crystals (4.6 g, 99%) (Scheme 2).

$^1$H NMR (300 MHz, DMSO-$d_6$): 0.23 (s, 6H), 0.96 (s, 9H), 6.98 (d, 2H, J=8.6 Hz), 7.19-7.31 (m, 4H), 7.84 (d, 2H, J=8.6 Hz), 8.52 (s, 1H).

Scheme 2.

Intermediate 2

Preparation of (3R,4R)-3-amino-1-(4-fluorophenyl)-4-(4-(t-butyldimethylsilyloxy)phenyl)azetidin-2-one (Intermediate 3)

Intermediate 3 was synthesized following the procedure described in Hart et. al. *J. Org Chem.* 1983, 48, 289; Ha et. al. *J. Am. Chem. Soc.* 1984, 106, 4819; Hart et. al. *Chem. Rev.* 1989, 89, 1447; Ojima et. al. *Tetrahedron Lett.* 1990, 31, 4289; Poljak et. al. *J. Mol. Struct.* 2005, 751, 60. The reaction was carried out in anhydrous conditions under argon atmosphere and the temperature at −78° C. To a solution of LDA (1.1 equivalent) in THF, 1-[(1R,2S,5R)-(−)-(menthyloxycarbonyl)methyl]-2,2,5,5-tetramethyl-2,5-disilyl-1-azacyclopentane (2.7 g, 7.51 mmol) dissolved in THF (4 mL) was added dropwise. The mixture was stirred for 10 minutes followed by a dropwise addition of intermediate 2 (2.5 g, 7.51 mmol) dissolved in THF (5 mL). After 20 h distilled water was added and the resulting mixture extracted with ethyl acetate (3×40 mL). Collected organic layers were dried over $Na_2SO_4$ and solvent evaporated to dryness. Intermediate 3 was purified by a silica gel column chromatography (hexane/ethyl acetate 9:1, gradually increasing the content of ethyl acetate in eluent to pure ethyl acetate) and obtained as yellow oil (1.3 g, 43%) (Scheme 3).

$^1$H NMR (600 MHz, CDCl$_3$): 0.19 (s, 6H), 0.97 (s, 9H), 1.81 (bs, 2H), 4.05 (d, 1H, J=2.2 Hz), 4.58 (d, 1H, J=2.1 Hz), 6.83 (d, 2H, J=8.5 Hz), 6.92 (t, 2H, J$_{1,2}$=8.7 Hz), 7.18 (d, 2H, J=8.5 Hz), 7.23-7.25 (m, 2H).

Scheme 3.

Intermediate 2

+

IVa $\xrightarrow{\text{LDA}}{\text{THF, -78° C.}}$

Intermediate 3

Preparation of (E)-1-[(3R,4R)-1-(4-fluorophenyl)-4-(4-(t-butyldimethylsilyloxy)phenyl)-2-oxo-3-azetidinylamino]-3-phenyl-2-propen-1-one (Intermediate 4a)

Reaction was carried out in dry conditions under argon atmosphere. To a solution of (3R,4R)-3-amino-1-(4-fluorophenyl)-4-(4-(t-butyldimethyl silyloxy)phenyl)azetidin-2-one (Intermediate 3, 63 mg, 0.16 mmol) in anhydrous CH$_2$Cl$_2$ (5 mL), Et$_3$N (6 equivalents) and (E)-3-phenylprop-2-enoyl chloride (55 mg, 0.33 mmol, 2 equivalents) were added (Scheme 4). The reaction mixture was refluxed overnight, then cooled to room temperature, distilled water added and the corresponding intermediate 4a extracted with CH$_2$Cl$_2$ (3×20 mL). Collected organic layers were dried over Na$_2$SO$_4$ and solvent evaporated to dryness. Intermediate 4a was isolated (43 mg, 51%) by a silica gel column chromatography (hexane/ethyl acetate 2:1).

$^1$H NMR (300 MHz, CDCl$_3$): 0.19 (s, 6H), 0.97 (s, 9H), 4.75 (dd, 1H, J$_1$=2.2 Hz, J$_2$=7.2 Hz), 5.04 (d, 1H, J=2.1 Hz), 6.46 (d, 1H, J=15.7 Hz), 6.80-6.88 (m, 4H), 7.17-7.22 (m, 4H), 7.30-7.32 (m, 4H), 7.38-7.42 (m, 2H), 7.58 (d, 1H, J=15.5 Hz).

(E)-1-[(3R,4R)-1-(4-fluorophenyl)-4-(4-(t-butyldimethylsilyloxy)phenyl)-2-oxo-3-azetidinylamino]-3-(4-fluorophenyl)-2-propen-1-one (Intermediate 4b)

According to the procedure for intermediate 4a, starting from intermediate 3 (62 mg, 0.16 mmol) and (E)-3-(-4-fluorophenyl)prop-2-enoyl chloride (59 mg, 0.32) intermediate 4b (43 mg, 49%) was obtained (Scheme 4).

$^1$H NMR (300 MHz, CDCl$_3$): 0.19 (s, 6H), 0.97 (s, 9H), 4.74 (dd, 1H, J$_1$=2.2 Hz, J$_2$=7.3 Hz), 5.07 (d, 1H, J=2.1 Hz), 6.37 (d, 1H, J=15.6 Hz), 6.80-6.88 (m, 4H), 6.98 (t, 2H, J$_{1,2}$=8.6 Hz), 0.7.16-7.21 (m, 4H), 7.32-7.37 (m, 2H), 7.42 (d, 1H, J=7.1 Hz), 7.48 (d, 1H, J=15.7 Hz).

1-[(3R,4R)-1-(4-fluorophenyl)-4-(4-(t-butyldimethylsilyloxy)phenyl)-2-oxo-3-azetidinylamino]-2-phenyl-ethan-1-one (Intermediate 4c)

According to the procedure for intermediate 4a, starting from intermediate 3 (44 mg, 0.11 mmol) and 2-phenylethanoyl chloride (35 mg, 0.22 mmol) intermediate 4c (22 mg, 38%) was obtained (Scheme 4).

$^1$H NMR (300 MHz, CDCl$_3$): 0.18 (s, 6H), 0.96 (s, 9H), 3.62 (s, 2H), 4.55 (dd, 1H, J$_1$=2.1 Hz, J$_2$=7.0 Hz), 4.85 (d, 1H, J=2.0 Hz), 6.50 (d, 1H, J=6.8 Hz), 6.79-6.88 (m, 4H), 7.13-7.17 (m, 4H), 7.25-7.35 (m, 5H).

1-[(3R,4R)-1-(4-fluorophenyl)-4-(4-(t-butyldimethylsilyloxy)phenyl)-2-oxo-3-azetidinylamino]-2-(4-fluorophenyl)-ethan-1-one (Intermediate 4d)

According to the procedure for intermediate 4a, starting from intermediate 3 (67 mg, 0.17 mmol) and 2-(4-fluorophenyl)ethanoyl chloride (60 mg, 0.35 mmol) intermediate 4d (41 mg, 45%) was obtained (Scheme 4).

$^1$H NMR (300 MHz, CDCl$_3$): 0.18 (s, 6H), 0.96 (s, 9H), 3.56 (s, 2H), 4.60 (dd, 1H, J$_1$=2.0 Hz, J$_2$=7.0 Hz), 4.83 (d, 1H, J=2.0 Hz), 6.73 (d, 1H, J=7.0 Hz), 6.79-6.87 (m, 4H), 7.01 (t, 2H, J$_{1,2}$=8.6 Hz), 7.11-7.16 (m, 4H), 7.21-7.25 (m, 2H).

[(3R,4R)-1-(4-fluorophenyl)-4-(4-(t-butyldimethylsilyloxy)phenyl)-2-oxo-3-azetidinylamino]phenyl-formaldehyde (Intermediate 4e)

According to the procedure for intermediate 4a, starting from intermediate 3 (46 mg, 0.12 mmol) and benzoyl chloride (33 mg, 0.24 mmol) intermediate 4e (35 mg, 60%) was obtained (Scheme 4).

$^1$H NMR (300 MHz, CDCl$_3$): 0.20 (s, 6H), 0.97 (s, 9H), 4.77 (dd, 1H, J$_1$=2.1 Hz, J$_2$=6.5 Hz), 5.09 (d, 1H, J=2.0 Hz), 6.85 (d, 2H, J=8.5 Hz), 6.90-6.96 (m, 3H), 7.26-7.30 (m, 4H), 7.42-7.47 (m, 2H), 7.51-7.56 (m, 1H), 7.80-7.82 (m, 2H).

[(3R,4R)-1-(4-fluorophenyl)-4-(4-(t-butyldimethylsilyloxy)phenyl)-2-oxo-3-azetidinylamino](4-fluorophenyl)formaldehyde (Intermediate 4f)

According to the procedure for intermediate 4a, starting from intermediate 3 (46 mg, 0.12 mmol) and 4-fluorobenzoyl chloride (38 mg, 0.24 mmol) intermediate 4f (25 mg, 41%) was obtained (Scheme 4).

$^1$H NMR (300 MHz, CDCl$_3$): 0.20 (s, 6H), 0.97 (s, 9H), 4.76 (dd, 1H, J$_1$=2.1 Hz, J$_2$=6.5 Hz), 5.07 (d, 1H, J=2.0 Hz), 6.85 (d, 2H, J=8.5 Hz), 6.90-6.96 (m, 3H), 7.12 (t, 2H, J$_{1,2}$=8.6 Hz), 7.23-7.29 (m, 4H), 7.80-7.85 (m, 2H).

Scheme 4.

Intermediate 3

Acyl chlorides

Intermediate 4a-f

4a, R$_x$ = (E)-C$_6$H$_5$—CH=CH—

4b, R$_x$ = (E)-(4-F—C$_6$H$_4$)—CH=CH—

4c, R$_x$ = C$_6$H$_5$—CH$_2$—

4d, R$_x$ = 4-F—C$_6$H$_4$—CH$_2$—

4e, R$_x$ = C$_6$H$_4$—

4f, R$_x$ = 4-F—C$_6$H$_4$—

Preparation of 2-[(3R,4R)-1-(4-fluorophenyl)-4-(4-(t-butyldimethylsilyloxy)phenyl)-2-oxo-3-azetidinylamino]-1-(4-fluorophenyl)ethan-1-one (Intermediate 5)

To a solution of (3R,4R)-3-amino-1-(4-fluorophenyl)-4-(4-(t-butyldimethylsilyloxy)phenyl)azetidin-2-one (Intermediate 3, 159 mg, 0.41 mmol) in the mixture of anhydrous THF and DMF (9:1, 7.8 mL), 2-bromo-1-(4-fluorophenyl)ethan-1-one (98 mg, 0.45 mmol), sodium iodide (68 mg, 0.45 mmol) and Et$_3$N (114 µL, 0.82 mmol) were added. The reaction mixture was stirred at room temperature for 3 h after which solvent was evaporated, distilled water (10 mL) added and the product extracted with ethyl acetate (3×20 mL). Collected organic layers were dried over Na$_2$SO$_4$ and solvent evaporated to dryness. Intermediate 5 was purified by a silica gel column chromatography (hexane/ethyl acetate 2:1) and obtained as light brown oil (99 mg, 46%) (Scheme 5).

$^1$H NMR (600 MHz, CDCl$_3$): 0.18 (s, 6H), 0.96 (s, 9H), 4.09 (d, 1H, J=2.1 Hz), 4.26, 4.34 (ABq, 2H, J$_{AB}$=18.5 Hz), 4.80 (d, 1H, J=1.9 Hz), 6.80 (d, 2H, J=8.5 Hz), 6.93 (t, 2H, J$_{1,2}$=8.6 Hz), 7.12-7.16 (m, 4H), 7.25-7.27 (m, 2H), 7.94-7.97 (m, 2H).

Scheme 5.

Intermediate 3

2-bromo-1-(4-fluorophenyl)ethan-1-one

NaI, Et$_3$N
THF:DMF 9:1, r.t., 3 h

Intermediate 5

Preparation of (1R)-2-bromo-1-(4-fluorophenyl)ethan-1-ol (Intermediate 6)

Reaction was carried out in dry conditions under argon atmosphere following the procedure described in Corey et. al. *J. Am. Chem. Soc.* 1987, 109, 7925 and Karlsson et. al. *Org. Process Res. Dev.* 2012, 16, 586. To a solution of (R)-(+)-2-methyl-CBS-oxazaborolidine catalyst (64 mg, 0.23 mmol) in anhydrous THF (2 mL), 2M THF solution of BH$_3$.Me$_2$S (1.15 mL, 2.30 mmol) was added. The mixture was stirred for 10 min and a solution of 2-bromo-1-(4-fluorophenyl)ethan-1-one (500 mg, 2.30 mmol) in anhydrous THF (4 mL) added dropwise (Scheme 6). The reaction proceeded at room temperature overnight after which the reaction mixture was quenched with methanol. Solvent was evaporated to dryness and distilled water (15 mL) added. The product was extracted with CH$_2$Cl$_2$ (3×30 mL), collected organic layers dried over Na$_2$SO$_4$ and solvent evaporated to dryness. Intermediate 6 was purified by a silica gel column chromatography (hexane/ethyl acetate 6:1) and obtained as colourless oil (503 mg, 100%). The ee>99% of intermediate 6 was determined by chiral HPLC (200/4 Nucleodex beta-PM Column, Macherey-Nagel, Germany, Method: 0.1% TEAA in H$_2$O:methanol 55:45, 30 min, flow 0.7 mL/min, λ=254 nm, retention time 19.5 min).

$^1$H NMR (300 MHz, CDCl$_3$): 2.75 (bs, 1H), 3.46-3.61 (m, 2H), 4.89 (dd, 1H, J$_1$=3.5 Hz, J$_2$=8.7 Hz), 7.05 (t, 2H, J$_{1,2}$=8.6 Hz), 7.32-7.37 (m, 2H).

Scheme 6.

Preparation of (1R)-2-bromo-1-(t-butyldimethylsilyloxy)-1-(4-fluorophenyl)ethane (Intermediate 7)

Reaction was carried out in dry conditions under argon atmosphere following the procedure described in Karlsson et. al. *Org. Process Res. Dev.* 2012, 16, 586. To a solution of (1R)-2-bromo-1-(4-fluorophenyl)ethan-1-ol (Intermediate 6, 327 mg, 1.49 mmol) in DMF (1 mL), a solution of imidazole (254 mg, 3.74 mmol) in DMF (0.5 mL) was added and stirred for 10 minutes followed by the addition of TBDMSCl solution (293 mg, 1.94 mmol) in DMF (1.3 mL). The reaction proceeded for 72 h at room temperature, solvent was evaporated to dryness and distilled water (15 mL) added. The resulting mixture was extracted with ethyl acetate (3×30 mL). Collected organic layers were dried over Na$_2$SO$_4$ and solvent evaporated to dryness. Intermediate 7 was purified by a silica gel column chromatography (hexane/ethyl acetate 6:1) and obtained as colourless oil (452 mg, 91%) (Scheme 7).

$^1$H NMR (300 MHz, CDCl$_3$): -0.09 (s, 3H), 0.10 (s, 3H), 0.88 (s, 9H), 3.36-3.48 (m, 2H), 4.82 (dd, 1H, J$_1$=4.8 Hz, J$_2$=7.4 Hz), 7.02 (t, 2H, J$_{1,2}$=8.7 Hz), 7.28-7.33 (m, 2H).

Scheme 7.

Preparation of (1R)-2-iodo-1-(t-butyldimethylsilyloxy)-1-(4-fluorophenyl)ethane (Intermediate 8)

Reaction was carried out in a reaction flask protected from light. To a solution of (1R)-2-bromo-1-(t-butyldimethylsilyloxy)-1-(4-fluorophenyl)ethane (Intermediate 7, 113 mg, 0.34 mmol) in acetone (3 mL), NaI (254 mg, 1.68 mmol) was added. The reaction proceeded at 55° C. for 4 days after which distilled water (15 mL) was added and the product extracted with ethyl acetate (3×30 mL). Collected organic layers were dried over Na$_2$SO$_4$ and solvent evaporated to dryness. Intermediate 8 was obtained as light brown oil (124 mg, 96%) (Scheme 8).

$^1$H NMR (300 MHz, CDCl$_3$): -0.13 (s, 3H), 0.10 (s, 3H), 0.89 (s, 9H), 3.28-3.30 (m, 2H), 4.73 (t, 1H, J$_{1,2}$=6.0 Hz), 7.00 (t, 2H, J$_{1,2}$=8.7 Hz), 7.26-7.31 (m, 2H).

Scheme 8.

Preparation of (3R,4R)-3-[(2R)-2-(4-fluorophenyl)-2-(t-butyldimethylsilyloxy) ethylamino]-1-(4-fluorophenyl)-4-(4-(t-butyldimethylsilyloxy)phenyl)azetidin-2-one (Intermediate 9)

Reaction was carried out in a reaction flask protected from light. To a solution of (3R,4R)-3-amino-1-(4-fluorophenyl)-4-(4-(t-butyldimethylsilyloxy)phenyl)azetidin-2-one (Intermediate 3, 154 mg, 0.40 mmol) in CH₃CN (2 mL), (1R)-2-iodo-1-(t-butyldimethylsilyloxy)-1-(4-fluorophenyl) ethane (Intermediate 8, 152 mg, 0.40 mmol) was added. The reaction proceeded at 80° C. for 7 days after which the solvent was evaporated to dryness. Intermediate 9 was purified by a silica gel column chromatography (hexane/ethyl acetate 6:1) and obtained as light brown oil (52 mg, 20%) (Scheme 9).

$^1$H NMR (300 MHz, CDCl$_3$): −0.15 (s, 3H), 0.02 (s, 3H), 0.18 (s, 6H), 0.86 (s, 9H), 0.96 (s, 9H), 2.78-2.99 (m, 2H), 4.00 (d, 1H, J=2.1 Hz), 4.61 (d, 1H, J=1.8 Hz), 4.77 (dd, 1H, J$_1$=4.3 Hz, J$_2$=7.8 Hz), 6.81 (d, 2H, J=8.7 Hz), 6.91 (t, 2H, J$_{1,2}$=8.8 Hz), 6.99 (t, 2H, J$_{1,2}$=8.8 Hz), 7.13 (d, 2H, J=8.5 Hz), 7.21-7.30 (m, 4H).

Intermediate 9

Preparation of (3R,4R)-3-amino-1-(4-fluorophenyl)-4-(4-hydroxyphenyl)azetidin-2-one (1)

To a solution of (3R,4R)-3-amino-1-(4-fluorophenyl)-4-(4-(t-butyldimethylsilyloxy)phenyl)azetidin-2-one (Intermediate 3, 56 mg, 0.14 mmol) in ethanol (3.5 mL) 1M HCl (800 µL) was added and the mixture stirred at room temperature overnight (Scheme 10). The reaction mixture was evaporated to dryness, 0.1 M HCl (10 mL) added and the resulting mixture extracted with ethyl acetate (1×20 mL). 2M NaOH was added to the water layer (pH 10), followed by the extraction of the product 1 with ethyl acetate (3×20 mL). Collected organic layers were dried over Na$_2$SO$_4$ and solvent evaporated to dryness. Product 1 was purified by a silica gel column chromatography (ethyl acetate) and obtained as white crystals (34 mg, 86%).

$^1$H NMR (600 MHz, DMSO-d$_6$): 2.47 (s, 1H), 3.88 (d, 1H, J=2.3 Hz), 4.62 (d, 1H, J=2.3 Hz), 6.75 (d, 2H, J=8.6 Hz), 7.12 (t, 2H, J$_{1,2}$=8.9 Hz), 7.17 (d, 2H, J=8.5 Hz), 7.21-7.23 (m, 2H), 9.45 (s, 1H).

Scheme 9.

Scheme 10.

Preparation of (E)-1-[(3R,4R)-1-(4-fluorophenyl)-4-(4-hydroxyphenyl)-2-oxo-3-azetidinylamino]-3-phenyl-2-propen-1-one (2)

To a 35 mM solution of intermediate 4a (87 mg, 0.17 mmol) in ethanol, 1M HCl (5.5 equivalent) was added and the mixture stirred at room temperature overnight (Scheme 11), distilled water (10 mL) was added and the resulting mixture extracted with ethyl acetate (3×20 mL). Collected organic layers were dried over $Na_2SO_4$ and solvent evaporated to dryness. After purification by a silica gel column chromatography (hexane/ethyl acetate 1:1), product 2 (55 mg, 80%) was obtained.

$^1$H NMR (300 MHz, DMSO-$d_6$): 4.74 (dd, 1H, $J_1$=2.4 Hz, $J_2$=7.9 Hz), 5.09 (d, 1H, J=2.4 Hz), 6.65 (d, 1H, J=15.8 Hz), 6.78 (d, 2H, J=8.3 Hz), 7.17 (t, 2H, $J_{1,2}$=8.8 Hz), 7.25-7.31 (m, 4H), 7.39-7.45 (m, 3H), 7.49 (d, 1H, J=15.8 Hz), 7.59-7.61 (m, 2H), 9.01 (d, 1H, J=7.9 Hz), 9.58 (s, 1H).

Preparation of (E)-1-[(3R,4R)-1-(4-fluorophenyl)-4-(4-hydroxyphenyl)-2-oxo-3-azetidinylamino]-3-(4-fluorophenyl)-2-propen-1-one (3)

According to the procedure for compound 2, starting from intermediate 4b (74 mg, 0.14 mmol) compound 3 (53 mg, 92%) was obtained (Scheme 11).

$^1$H NMR (300 MHz, DMSO-$d_6$): 4.74 (dd, 1H, $J_1$=2.4 Hz, $J_2$=8.1 Hz), 5.08 (d, 1H, J=2.3 Hz), 6.60 (d, 1H, J=16.0 Hz), 6.78 (d, 2H, J=8.3 Hz), 7.17 (t, 2H, $J_{1,2}$=8.8 Hz), 7.23-7.31 (m, 6H), 7.49 (d, 1H, J=16.0 Hz), 7.64-7.69 (m, 2H), 9.00 (d, 1H, J=7.9 Hz), 9.59 (s, 1H).

Preparation of 1-[(3R,4R)-1-(4-fluorophenyl)-4-(4-hydroxyphenyl)-2-oxo-3-azetidinylamino]-2-phenyl-ethan-1-one (4)

According to the procedure for compound 2, starting from intermediate 4c (40 mg, 0.08 mmol) compound 4 (27 mg, 88%) was obtained (Scheme 11).

$^1$H NMR (300 MHz, DMSO-$d_6$): 3.56 (s, 2H), 4.60 (dd, 1H, $J_1$=2.2 Hz, $J_2$=7.6 Hz), 4.91 (d, 1H, J=2.0 Hz), 6.79 (d, 2H, J=8.5 Hz), 6.92 (t, 2H, $J_{1,2}$=8.7 Hz), 7.13 (d, 2H, J=8.3 Hz), 7.22-7.32 (m, 7H), 8.51 (d, 1H, J=7.9 Hz), 9.15 (s, 1H).

Preparation of 1-[(3R,4R)-1-(4-fluorophenyl)-4-(4-hydroxyphenyl)-2-oxo-3-azetidinylamino]-2-(4-fluorophenyl)-ethan-1-one (5)

According to the procedure for compound 2, starting from intermediate 4d (77 mg, 0.15 mmol) compound 5 (51 g, 84%) was obtained (Scheme 11).

$^1$H NMR (600 MHz, DMSO-$d_6$): 3.52 (s, 2H), 4.60 (dd, 1H, $J_1$=2.5 Hz, $J_2$=7.9 Hz), 4.98 (d, 1H, J=2.4 Hz), 6.76 (d, 2H, J=8.6 Hz), 7.12-7.15 (m, 4H), 7.22-7.24 (m, 4H), 7.28-7.31 (m, 2H), 8.87 (d, 1H, J=8.0 Hz), 9.54 (s, 1H).

Preparation of [(3R,4R)-1-(4-fluorophenyl)-4-(4-hydroxyphenyl)-2-oxo-3-azetidinylamino] phenylformaldehyde (6)

According to the procedure for compound 2, starting from intermediate 4e (62 mg, 0.13 mmol) compound 6 (35 mg, 74%) was obtained (Scheme 11).

$^1$H NMR (600 MHz, DMSO-$d_6$): 4.79 (dd, 1H, $J_1$=2.6 Hz, $J_2$=8.0 Hz), 5.15 (d, 1H, J=2.5 Hz), 6.78 (d, 2H, J=8.7 Hz), 7.17 (t, 2H, $J_{1,2}$=8.9 Hz), 7.27-7.29 (m, 2H), 7.31 (d, 2H, J=8.6 Hz), 7.50 (t, 2H, $J_{1,2}$=7.7 Hz), 7.56-7.59 (m, 1H), 7.88-7.90 (m, 2H), 9.31 (d, 1H, J=8.1 Hz), 9.56 (s, 1H).

Preparation of [(3R,4R)-1-(4-fluorophenyl)-4-(4-hydroxyphenyl)-2-oxo-3-azetidinylamino](4-fluorophenyl)formaldehyde (7)

According to the procedure for compound 2, starting from intermediate 4f (81 mg, 0.16 mmol) compound 7 (45 mg, 71%) was obtained (Scheme 11).

$^1$H NMR (300 MHz, DMSO-$d_6$): 4.81 (d, 1H, J=7.9 Hz), 5.08 (s, 1H), 6.82 (d, 2H, J=7.7 Hz), 6.98 (t, 2H, $J_{1,2}$=8.2 Hz), 7.13 (t, 2H, $J_{1,2}$=8.4 Hz), 7.21 (d, 2H, J=7.9 Hz), 7.28-7.32 (m, 2H), 7.95-7.99 (m, 2H), 9.17 (d, 1H, J=7.7 Hz), 9.25 (s, 1H).

Scheme 11.

Intermediate 4a-f

-continued

2, $R_x$ = (E)-$C_6H_5$—CH=CH—
3, $R_x$ = (E)-(4-F—$C_6H_4$)—CH=CH—
4, $R_x$ = $C_6H_5$—$CH_2$—
5, $R_x$ = 4-F—$C_6H_4$—$CH_2$—
6, $R_x$ = $C_6H_5$—
7, $R_x$ = 4-F—$C_6H_4$—

Preparation of diastereoisomeric mixture of (3R, 4R)-3-[(2R/S)-2-(4-fluorophenyl)-2-hydroxyethyl-amino]-1-(4-fluorophenyl)-4-(4-hydroxyphenyl) azetidin-2-one (8/9)

Reduction of 2-[(3R,4R)-1-(4-fluorophenyl)-4-(4-(t-butyldimethylsilyloxy)phenyl)-2-oxo-3-azetidinylamino]-1-(4-fluorophenyl)ethan-1-one (Intermediate 5) was performed following a modified Corey's procedure in Masui et. al. *Synlett,* 1997, 3, 273; Quallich et. al. *Tetrahedron Lett.* 1993, 34, 785 and Wu et. al. *J. Org. Chem.* 1999, 64, 3714. The reaction was carried out in dry conditions under argon atmosphere. To a solution of (R)-(+)-2-methyl-CBS-oxazaborolidine catalyst (251 mg, 0.91 mmol) in anhydrous THF (2 mL), 2M THF solution of $BH_3.Me_2S$ (454 µL, 0.91 mmol) was added and the mixture stirred at room temperature for 10 min. The reaction mixture was then cooled to −20° C., followed by the addition of a solution of intermediate 5 (474 mg, 0.91 mmol) in anhydrous THF (5 mL). After 24 h the reaction mixture was warmed to room temperature and quenched with methanol. The solution was concentrated in vacuo and distilled water (15 mL) added followed by the extraction with ethyl acetate (3×40 mL). Collected organic layers were dried over $Na_2SO_4$ and solvent evaporated to dryness. Crude product was dissolved in ethanol (22 mL) and 1M HCl (5 mL) was added and stirred at room temperature overnight, solvent was evaporated to dryness and crude product purified by a silica gel column chromatography (hexane/ethyl acetate 1:3) to afford a diastereoisomeric mixture of 8 and 9 in ratio 70:30 (283 mg, 76%) (Scheme 12).

$^1$H NMR (300 MHz, $CDCl_3$): 2.85-3.06 (m, 2H, S+R), 4.00 (d, 1H, J=2.2 Hz, R-70), 4.03 (d, 1H, J=2.2 Hz, S-30), 4.67-4.70 (m, 2H, S+R), 4.78 (dd, 1H, $J_1$=3.6 Hz, $J_2$=8.7 Hz, R-70), 6.83 (d, 2H, J=8.5 Hz, S+R), 6.93 (t, 2H, $J_{1,2}$=8.7 Hz, S+R), 7.02 (t, 2H, $J_{1,2}$=8.7 Hz, S+R), 7.19 (d, 2H, J=8.5 Hz, S+R), 7.18-7.34 (m, 4H, S+R).

Scheme 12.

Intermediate 5

Preparation of diastereoisomeric mixture of (3R, 4R)-3-[(2S/R)-2-(4-fluorophenyl)-2-hydroxyethylamino]-1-(4-fluorophenyl)-4-(4-hydroxyphenyl)azetidin-2-one (9/8)

Reduction of 2-[(3R,4R)-1-(4-fluorophenyl)-4-(4-(t-butyldimethylsilyloxy)phenyl)-2-oxo-3-azetidinylamino]-1-(4-fluorophenyl)ethan-1-one (Intermediate 5) was performed following a modified Corey's procedure described in Masui et. al. *Synlett*, 1997, 3, 273; Quallich et. al. *Tetrahedron Lett.* 1993, 34, 785 and Wu et. al. *J. Org. Chem.* 1999, 64, 3714. The reaction was carried out in dry conditions under argon atmosphere. To a solution of (S)-(−)-2-methyl-CBS-oxazaborolidine catalyst (275 mg, 0.99 mmol) in anhydrous THF (2 mL) 2M THF solution of $BH_3.Me_2S$ (496 µL, 0.99 mmol) was added and the mixture stirred at room temperature for 10 min. The reaction mixture was then cooled to −20° C., followed by the addition of a solution of intermediate 5 (519 mg, 0.99 mmol) in anhydrous THF (5 mL). After 24 h the reaction mixture was warmed to room temperature and quenched with methanol. The solution was concentrated in vacuo and distilled water (15 mL) added, followed by extraction with ethyl acetate (3×40 mL). Collected organic layers were dried over $Na_2SO_4$ and solvent evaporated to dryness. Crude product was dissolved in ethanol (24 mL) and 1M HCl (5.5 mL) was added and stirred at room temperature overnight, solvent evaporated to dryness and crude product purified by a silica gel column chromatography (hexane/ethyl acetate 1:3) to give a diastereomeric mixture of 9 and 8 in ratio 85:15 (278 mg, 68%) (Scheme 13).

$^1$H NMR (600 MHz, $CDCl_3$): 2.88-3.04 (m, 2H, S+R), 4.00 (d, 1H, J=2.0 Hz, R-15), 4.03 (d, 1H, J=1.9 Hz, S-85), 4.68-4.70 (m, 2H, S+R), 4.78 (dd, 1H, $J_1$=3.6 Hz, $J_2$=8.6 Hz, R-15), 6.84 (d, 2H, J=8.5 Hz, S+R), 6.93 (t, 2H, $J_{1,2}$=8.7 Hz, S+R), 7.02 (t, 2H, $J_{1,2}$=8.7 Hz, S+R), 7.19 (d, 2H, J=8.5 Hz, S+R), 7.23-7.25 (m, 2H, S+R), 7.29-7.31 (m, 2H, S+R).

Scheme 13.

Intermediate 5

9/8; 9

(3R,4R)-3-[(2S)-2-(4-fluorophenyl)-2-hydroxyethylamino]-1-(4-fluorophenyl)-4-(4-hydroxyphenyl)azetidin-2-one (9)

Diastereoisomere 9 was obtained (111 mg, 25%) by recrystallization of the diastereoisomeric mixture of 9 and 8 in ratio 85:15 in $CH_2Cl_2$.

$^1$H NMR (300 MHz, DMSO-$d_6$): 2.70-2.86 (m, 2H), 3.97 (d, 1H, J=1.9 Hz), 4.54-4.59 (m, 1H), 4.84 (d, 1H, J=1.9 Hz), 5.38 (d, 1H, J=4.3 Hz), 6.75 (d, 2H, J=8.5 Hz), 7.07-7.25 (m, 8H), 7.30-7.34 (m, 2H), 9.48 (s, 1H).

(3R,4R)-3-[(2R)-2-(4-fluorophenyl)-2-hydroxyethylamino]-1-(4-fluorophenyl)-4-(4-hydroxyphenyl)azetidin-2-one (8)

(3R,4R)-3-[(2R)-2-(4-fluorophenyl)-2-(t-butyldimethylsilyloxy)ethylamino]-1-(4-fluorophenyl)-4-(4-(t-butyldimethylsilyloxy)phenyl)azetidin-2-one (Intermediate 9, 24 mg, 0.04 mmol) was dissolved in 3% HCl in ethanol (90 µL conc. HCl in 1.5 mL ethanol) and the mixture was stirred at room temperature overnight. Solvent was evaporated to dryness and crude product purified by a silica gel column chromatography (hexane/ethyl acetate 1:3, 5% MeOH). Product 8 was obtained as light yellow powder (13 mg, 84%) (Scheme 14).

$^1$H NMR (300 MHz, CDCl$_3$): 2.86-3.02 (m, 2H), 4.00 (d, 1H, J=2.0 Hz), 4.70 (d, 1H, J=1.8 Hz), 4.78 (dd, 1H, J$_1$=3.6 Hz, J$_2$=8.6 Hz), 6.81 (d, 2H, J=8.6 Hz), 6.91 (t, 2H, J$_{1,2}$=8.8 Hz), 7.00 (t, 2H, J$_{1,2}$=8.8 Hz), 7.15 (d, 2H, J=8.4 Hz), 7.19-7.34 (m, 4H).

Scheme 14.

Preparation of N-[(3R,4R)-1-(4-fluorophenyl)-4-(4-hydroxyphenyl)-2-oxo-3-azetidinyl]-(2R)-2-hydroxy-2-(4-fluorophenyl)ethylammonium chloride (10)

14 mg (0.034 mmol) of compound 8 was dissolved in ethanol (1 mL) followed by addition of 1M HCl (44 μL). The mixture was stirred for 1 h at 0° C. Ethanol was evaporated to dryness to afford compound 10 (15 mg, 100%) (Scheme 15).

$^1$H NMR (300 MHz, DMSO-d$_6$): 3.14-3.33 (2H, m), 4.63 (1H, s), 4.97 (1H, d, J=8.2 Hz), 5.28 (1H, s), 6.29 (1H, bs), 6.78 (2H, d, J=8.6 Hz), 7.17-7.28 (6H, m), 7.34 (2H, d, J=8.5 Hz), 7.40-7.45 (2H, m), 9.71 (1H, bs), 10.20 (1H, bs), 10.38 (1H, bs).

Preparation of N-[(3R,4R)-1-(4-fluorophenyl)-4-(4-hydroxyphenyl)-2-oxo-3-azetidinyl]-(2S)-2-hydroxy-2-(4-fluorophenyl)ethylammonium chloride (11)

According to the procedure for compound 10, starting from 9 (15 mg, 0.036 mmol) compound 11 (16 mg, 100%) was obtained (Scheme 15).

$^1$H NMR (600 MHz, DMSO-d$_6$): 3.21-3.33 (2H, m), 4.65 (1H, s), 4.99 (1H, d, J=8.7 Hz), 5.25 (1H, s), 6.29 (1H, bs), 6.80 (2H, d, J=8.6 Hz), 7.18-7.26 (6H, m), 7.35 (2H, d, J=8.6 Hz), 7.41-7.43 (2H, m), 9.68 (1H, bs), 10.13 (1H, bs), 10.47 (1H, bs).

Preparation of N-[(3R,4R)-1-(4-fluorophenyl)-4-(4-hydroxyphenyl)-2-oxo-3-azetidinyl]-(2R/S)-2-hydroxy-2-(4-fluorophenyl)ethylammonium chloride (10/11)

According to the procedure for compound 10, starting from diastereoisomeric mixture of 8/9-70/30 (17 mg, 0.041 mmol) diastereoisomeric mixture of 10/11-70/30 (18 mg, 100%) was obtained as hydrochloride salt (Scheme 15).

$^1$H NMR (600 MHz, DMSO-d$_6$): 3.16-3.33 (2H, m, S+R), 4.61 (1H, s, R-70), 4.65 (1H, s, S-30), 4.96 (1H, d, J=8.7 Hz, S+R), 5.23 (1H, s, S-30), 5.26 (1H, s, R-70), 6.24 (1H, bs, S+R), 6.77-6.80 (2H, m, S+R), 7.17-7.27 (6H, m, S+R), 7.32-7.35 (2H, m, S+R), 7.41-7.43 (2H, m, S+R), 9.65 (1H, bs, S+R), 10.13 (1H, bs, S+R), 10.38 (1H, bs, S+R).

Preparation of N-[(3R,4R)-1-(4-fluorophenyl)-4-(4-hydroxyphenyl)-2-oxo-3-azetidinyl]-(2S/R)-2-hydroxy-2-(4-fluorophenyl)ethylammonium chloride (11/10)

According to the procedure for compound 10, starting from diastereoisomeric mixture of 9/8-85/15 (16 mg, 0.040 mmol) diastereoisomeric mixture of 11/10-85/15 (17 mg, 100%) was obtained as hydrochloride salt (Scheme 15).

$^1$H NMR (300 MHz, DMSO-d$_6$): 3.14-3.33 (2H, m, S+R), 4.63 (1H, s, R-15), 4.67 (1H, s, S-85), 4.97-5.02 (1H, m, S+R), 5.26 (1H, d, J=1.5 Hz, S-85), 5.29 (1H, d, J=1.2 Hz, R-15), 6.34 (1H, bs, S+R), 6.77-6.81 (2H, m, S+R), 7.17-7.28 (6H, m, S+R), 7.33-7.37 (2H, m, S+R), 7.40-7.45 (2H, m, S+R), 9.73 (1H, bs, S+R), 10.13 (1H, bs, S+R), 10.48 (1H, bs, S+R).

Scheme 15.

-continued

10/11; 11/10

The invention claimed is:

1. A compound of Formula (Ia) or (Ib):

1a

1b wherein R represents
a) hydrogen;
b) —C(=O)—C$_{1-6}$alkyl-C$_6$H$_4$R$^3$, —C(=O)—C$_{1-6}$alkenyl-C$_6$H$_4$R$^3$ or —C(=O)—C$_6$H$_4$R$^3$;
c) —C$_{1-6}$alkyl-C$_6$H$_4$R$^3$ or —C$_{1-6}$alkenyl-C$_6$H$_4$R$^3$, wherein said —C$_{1-6}$alkyl or —C$_{1-6}$alkenyl is substituted by OH;

R$^1$ represents OH or —OMe;
R$^2$ represents a halogen;
R$^3$ represents hydrogen, a halogen, —OMe, —NO$_2$ or —OH;
or a salt thereof.

2. A compound according to the claim 1 represented by Formula (Ia):

1a wherein
R represents
a) hydrogen;
b) —C(=O)—C$_{1-6}$alkyl-C$_6$H$_4$R$^3$, —C(=O)—C$_{1-6}$alkenyl-C$_6$H$_4$R$^3$ or —C(=O)—C$_6$H$_4$R$^3$;
c) —C$_{1-6}$alkyl-C$_6$H$_4$R$^3$ or —C$_{1-6}$alkenyl-C$_6$H$_4$R$^3$, wherein said —C$_{1-6}$alkyl or —C$_{1-6}$alkenyl is substituted by OH;
R$^1$ represents OH or —OMe;
R$^2$ represents a halogen;
R$^3$ represents hydrogen, a halogen, —OMe, —NO$_2$ or —OH;
or a salt thereof.

3. A compound according to claim 1, wherein R$^1$ represents —OH.

4. A compound according to claim 1, wherein R$^3$ represents hydrogen or a halogen.

5. A compound according to claim 1, wherein R represents hydrogen.

6. A compound according to claim 1, wherein R represents —C(=O)—C$_{1-6}$alkyl-C$_6$H$_4$R$^3$, —C(=O)—C$_{1-6}$alkenyl-C$_6$H$_4$R$^3$ or —C(=O)—C$_6$H$_4$R$^3$.

7. A compound according to the claim 6, wherein R represents —C(=O)—CH$_2$—C$_6$H$_4$R$^3$.

8. A compound according to the claim 6, wherein R represents —C(=O)—CH=CH—C$_6$H$_4$R$^3$.

9. A compound according to the claim 6, wherein R represents —C(=O)—C$_6$H$_4$R$^3$.

10. A compound according to claim 6, wherein R$^3$ represents hydrogen or a halogen.

11. A compound according to claim 1, wherein R represents —C$_{1-6}$alkyl-C$_6$H$_4$R$^3$ or C$_{1-6}$alkenyl-C$_6$H$_4$R$^3$ wherein said —C$_{1-6}$alkyl or —C$_{1-6}$alkenyl is substituted by OH.

12. A compound according to the claim 11, wherein R represents —CH$_2$—CH(OH)—C$_6$H$_4$R$^3$.

13. A compound according to the claim 12, wherein R$^3$ represents a halogen.

14. A compound of Formula (Ia) according to the claim 1 selected from:
(3R,4R)-3-amino-1-(4-fluorophenyl)-4-(4-hydroxyphenyl)azetidin-2-one (1);
(E)-1-[(3R,4R)-1-(4-fluorophenyl)-4-(4-hydroxyphenyl)-2-oxo-3-azetidinylamino]-3-phenyl-2-propen-1-one (2);
(E)-1-[(3R,4R)-1-(4-fluorophenyl)-4-(4-hydroxyphenyl)-2-oxo-3-azetidinylamino]-3-(4-fluorophenyl)-2-propen-1-one (3);
1-[(3R,4R)-1-(4-fluorophenyl)-4-(4-hydroxyphenyl)-2-oxo-3-azetidinylamino]-2-phenyl-ethan-1-one (4);
1-[(3R,4R)-1-(4-fluorophenyl)-4-(4-hydroxyphenyl)-2-oxo-3-azetidinylamino]-2-(4-fluorophenyl)-ethan-1-one (5);

[(3R,4R)-1-(4-fluorophenyl)-4-(4-hydroxyphenyl)-2-oxo-3-azetidinylamino]phenylformaldehyde (6);

[(3R,4R)-1-(4-fluorophenyl)-4-(4-hydroxyphenyl)-2-oxo-3-azetidinylamino](4-fluorophenyl)formaldehyde (7);

(3R,4R)-3-[(2R)-2-(4-fluorophenyl)-2-hydroxyethylamino]-1-(4-fluorophenyl)-4-(4-hydroxyphenyl)azetidin-2-one (8);

(3R,4R)-3-[(2S)-2-(4-fluorophenyl)-2-hydroxyethylamino]-1-(4-fluorophenyl)-4-(4-hydroxyphenyl)azetidin-2-one (9);

or a salt thereof.

15. A compound of Formula (Ia) according to the claim 1 selected from:

N-[(3R,4R)-1-(4-fluorophenyl)-4-(4-hydroxyphenyl)-2-oxo-3-azetidinyl]-(2R)-2-hydroxy-2-(4-fluorophenyl)ethylammonium chloride (10);

N-[(3R,4R)-1-(4-fluorophenyl)-4-(4-hydroxyphenyl)-2-oxo-3-azetidinyl]-(2S)-2-hydroxy-2-(4-fluorophenyl)ethylammonium chloride (11).

16. A compound of Formula (Ia) or (Ib) or a salt thereof according to claim 1, wherein the salt is pharmaceutically acceptable salt.

17. A pharmaceutical composition comprising a compound of Formula (Ia) or (Ib) as claimed in claim 1 or a pharmaceutically acceptable salt thereof and one or more pharmaceutically acceptable carriers.

18. A pharmaceutical composition according to claim 17, wherein the composition is enteric-coated.

19. A method for reducing cholesterol levels in a patient in need thereof, said method comprising administering an effective amount of a compound of claim 1, or a composition comprising an effective amount of a compound of claim 1, to reduce high cholesterol levels in the patient or treat atherosclerosis in the patient.

20. A compound of Formula (Ia) according to the claim 1 diastereomeric mixture of the:

(3R,4R)-3-[(2R/S)-2-(4-fluorophenyl)-2-hydroxyethylamino]-1-(4-fluorophenyl)-4-(4-hydroxyphenyl)azetidin-2-one, where the ratio between R and S diastereomers is 70:30 or 15:85;

or a salt thereof.

21. A compound of Formula (Ia) according to the claim 1 selected from the diastereomeric mixture of the:

N-[(3R,4R)-1-(4-fluorophenyl)-4-(4-hydroxyphenyl)-2-oxo-3-azetidinyl]-(2R/S)-2-hydroxy-2-(4-fluorophenyl)ethylammonium chloride, where the ratio between R and S diastereomers is 70:30 or 15:85.

* * * * *